United States Patent
De Diego

(10) Patent No.: US 9,725,458 B2
(45) Date of Patent: Aug. 8, 2017

(54) NALMEFENE SALTS AS MEDICAMENTS FOR REDUCING ALCOHOL CONSUMPTION OR FOR PREVENTING EXCESSIVE ALCOHOL CONSUMPTION

(71) Applicant: H. Lundbeck A/S, Valby (DK)

(72) Inventor: Heidi Lopez De Diego, Nærum (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 14/903,384

(22) PCT Filed: Jul. 10, 2014

(86) PCT No.: PCT/EP2014/064819
§ 371 (c)(1),
(2) Date: Jan. 7, 2016

(87) PCT Pub. No.: WO2015/004240
PCT Pub. Date: Jan. 15, 2015

(65) Prior Publication Data
US 2016/0152625 A1    Jun. 2, 2016

(30) Foreign Application Priority Data
Jul. 11, 2013  (DK) ................. 2013 00421

(51) Int. Cl.
*C07D 489/08* (2006.01)
*A61K 31/485* (2006.01)
(52) U.S. Cl.
CPC .................. *C07D 489/08* (2013.01)
(58) Field of Classification Search
CPC ........................ C07D 489/08; A61K 31/485
USPC .......................................... 546/44; 514/282
See application file for complete search history.

(56) References Cited

U.S. PATENT DOCUMENTS 8,598,352 B2 * 12/2013 De Faveri ............ C07D 489/08
546/44
2003/0153590 A1   8/2003 Kurkela et al.

FOREIGN PATENT DOCUMENTS

| CN | 103012416 | 4/2013 |
| WO | 2010/013044 | 2/2010 |
| WO | 2010/063292 | 6/2010 |

OTHER PUBLICATIONS

International Search Report PCT/EP2014/064819 (WO 2015/004240) (2014) (4 Pages).
Brittain, H.G. (1996) "*Nalmefene Hydrochloride*," In: Analytical Profiles of Drug Substances and Excipients, vol. 24, pp. 351-395.
CN103012416 (Machine English Translation) (2013) 3 pages.
Written Opinion of the Intellectual Property Office of Singapore for SG Patent Application No. 11201600116V (H. Lundbeck A/S) (2016) 6 pages.

* cited by examiner

*Primary Examiner* — Charanjit Aulakh
(74) *Attorney, Agent, or Firm* — Jeffrey L. Auerbach; AuerbachSchrot LLC

(57) ABSTRACT

The present invention relates to new nalmefene salts which salts fall within at least one of the two following categories: non-hydrate forming salts and non-solvate forming salts. In particular, the invention relates to the hydrogen adipate salt, the hydrogen malonate salt, the lactate salt, the hydrogen fumarate salt, the hydrogen succinate salt, the benzene sulfonate salt, the hydrogen maleate salt and the salicylate salt of nalmefene. The present invention also relates to such salts for use in therapy.

14 Claims, 17 Drawing Sheets

NALMEFENE SALTS AS MEDICAMENTS FOR REDUCING ALCOHOL CONSUMPTION OR FOR PREVENTING EXCESSIVE ALCOHOL CONSUMPTION

CROSS REFERENCE TO RELATED APPLICATIONS AND CLAIM TO PRIORITY

The present application is a §371 National Stage Application of PCT/EP2014/064819 (filed on Jul. 10, 2014; pending), which application claims priority to Denmark Patent Application No. PA201300421 (filed on Jul. 11, 2013), each of which applications is herein incorporated by reference in its entirety.

FIELD OF THE INVENTION

The present invention relates to new nalmefene salts which salts fall within at least one of the two following categories: non-hydrate forming salts and non-solvate forming salts. In particular, the invention relates to the hydrogen adipate salt, the hydrogen malonate salt, the lactate salt, the hydrogen fumarate salt, the hydrogen succinate salt, the benzene sulfonate salt, the hydrogen maleate salt and the salicylate salt of nalmefene. The present invention also relates to such salts for use in therapy.

BACKGROUND OF THE INVENTION

Nalmefene [17-(cyclopropylmethyl)-4,5-alpha-epoxy-6-methylenemorphinan-3,14-diol] has the following general formula:

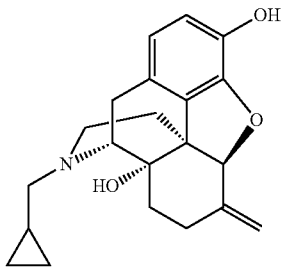

and can be prepared using methods that are well known in the art e.g. starting by manufacturing of naltrexone from noroxymorphone as described in WO 2012/059103 and subsequently manufacturing nalmefene from naltrexone e.g. by the Wittig reaction as described in WO 2010/136039.

Nalmefene is an opioid system modulator with a distinct μ, δ, and κ receptor profile. In vitro studies have demonstrated that nalmefene is a selective opioid receptor ligand with antagonist activity at the μ and δ receptors and partial agonist activity at the κ receptor. Acute alcohol intake was shown to result in mesolimbic dopamine release (facilitated by the release of β-endorphins), which can provide positive reinforcement. Nalmefene is thought to counteract the reinforcement effects and to reduce alcohol consumption, possibly by modulating these cortico-mesolimbic functions.

The efficacy and tolerability of nalmefene in the treatment of alcohol dependence have been evaluated in three phase III studies (two confirmatory 6-month efficacy studies and one 1-year safety study) conducted by Lundbeck (Mann et al. Extending the Treatment Options in Alcohol Dependence: A Randomized Controlled Study of As-Needed Nalmefene. *Biol Psychiatry* (2013); 73(8): 706-713; Gual et al. A randomised, double-blind, placebo-controlled, efficacy study of nalmefene, as-needed use, in patients with alcohol dependence. *European Neuropsychopharmacology* (2013); 23(11): 1432-1442; van den Brink et al., Long-term efficacy, tolerability and safety of nalmefene as-needed in patients with alcohol dependence: A 1-year, randomised controlled study. *J. Psychopharmacol.*, published online before print Mar. 26, 2014, doi: 10.1177/0269881114527362) and 5 studies in alcohol use disorders conducted by the company Biotie (Karhuvaara et al. *Alcohol. Clin Exp Res*. (2007); 31: 1179-1187).

A marketing authorization was granted in February 2013 in the European Union (EU) for oral nalmefene under the tradename Selincro® for the reduction of alcohol consumption in adult patients with alcohol dependence.

The only known salt of nalmefene is the hydrochloride salt. Said nalmefene hydrochloride salt has been described as a hydrate-forming salt and known forms are nalmefene hydrochloride monohydrate (Brittain, H. G., *Analytical Profiles of Drug Substances and Excipients;* 1996, Vol. 24: 351-395) and nalmefene hydrochloride dihydrate (WO 2010/063292). Methods for obtaining said nalmefene hydrochloride monohydrate and dihydrate from crude nalmefene hydrochloride are described in WO 2010/063292.

It has not been possible to obtain a stable anhydrous form of Nalmefene hydrochloride as formation of anhydrous material by dehydration of a hydrate lead to hygroscopic material that absorbs water under transformation to a hydrate, and crystallization from ethanol lead to ethanol solvate (Brittain, H. G., *Analytical Profiles of Drug Substances and Excipients;* 1996, Vol. 24: 351-395 and WO 2010/063292).

There is a need for new salts of nalmefene with improved properties e.g. for chemical processing and for pharmaceutical formulation and storage.

SUMMARY OF THE INVENTION

The invention provides new nalmefene salts which possess at least one of the following properties: non-solvate forming and non-hydrate forming.

The present invention relates to a salt of the compound of formula [I]

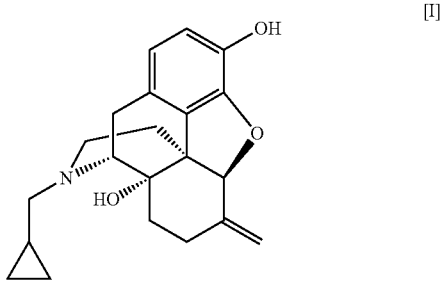 [SMILES: C=C1CC[C@@]2(O)[C@H]3Cc4ccc(O)c5c4[C@@]2(CCN3CC2CC2)[C@H]1O5]

wherein said salt falls within at least one of the two following categories:
a) non-hydrate forming salt;
b) non-solvate forming salt.

In one embodiment, the invention relates to a pharmaceutical composition comprising a salt of the present invention.

In one embodiment, the invention relates to a salt of the present invention for use in therapy.

In one embodiment, the invention relates to a salt of the present invention for use in reduction of alcohol consumption in a patient with alcohol dependence.

BRIEF DESCRIPTION OF DRAWINGS

X-ray powder diffractograms (XRPDs) according to FIGS. 1-8 are obtained using $CuK_{\alpha 1}$ radiation ($\lambda=1.5406$ Å). The y-axis shows the intensity (counts) and the x-axis shows the 2θ-angles (°).

DEFINITIONS

Figure 1:
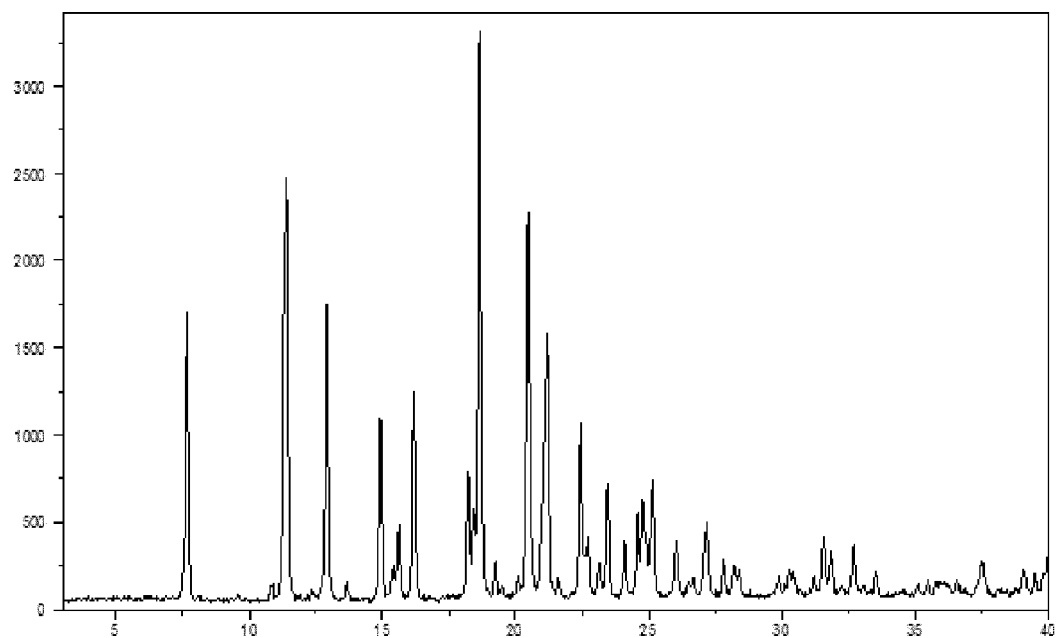
FIG. 1: XRPD pattern of the hydrogen adipate salt of nalmefene.

In the present context, a "non-solvate forming salt" of Nalmefene indicates a salt that generally does not form solvates when precipitated from various organic solvents e.g. EtOH, MeOH, IPA, EtOAc, acetone, ACN, THF, MIBK, toluene and 2,2,2-trifluoroethanol. In particular, said salts are non-solvate forming when solvent molecules do not form part of the crystal lattice of the salts precipitated from different solvents at atmospheric pressure and room temperature such as in a temperature range between 15-30° C., such as between 20-25° C. A "solvate" indicates a crystalline material with solvent molecules incorporated into the crystal lattice. In the present context, when referring to "solvents" these are limited to non-aqueous solvents, preferably organic solvents. Solvents assessed for solvate formation according to the invention includes the following: ethanol (EtOH), methanol (MeOH), isopropanol (IPA), ethyl acetate (EtOAc), acetone, acetonitrile (ACN), tetrahydrofurane (THF), methyl isobutyl ketone (MIBK), toluene and 2,2,2-trifluoroethanol.

In the present context, a "non-hydrate forming salt" of nalmefene indicates a salt that does not form a hydrate when precipitated from an aqueous solution such as water. In particular, said salts are non-hydrate forming when water molecules do not form part of the crystal lattice of the salt precipitated from water at atmospheric pressure and room temperature such as in a temperature range between 15-30° C., such as between 20-25° C. A "hydrate" indicates a crystalline material with water ($H_2O$) molecules incorporated into the crystal lattice. More particularly, a "non-hydrate forming salt" of nalmefene indicates a salt of which any isolated crystal form contains less than 25 mol % water, such as less than 20 mol % water, such as less than 15 mol % water, such as less than 10 mol % water, such as less than 5 mol % water, such as less than 4, 3, 2 or 1 mol % water, such as substantially no water in the crystal lattice of said salt.

In the present context, an "aqueous solution" is a solution comprising an essential amount of water such as a solution comprising at least 50% water, such as at least 60, 70, 80 or 90% water, such as at least 95 or 99% water, such as a solution comprising pure water.

Throughout the application "salts of the present invention" or "nalmefene salts of the present invention" indicates a nalmefene salt, which salt falls within at least one of the two following categories: a) non-hydrate forming salt; b) non-solvate forming salt. The salts of the present invention are all acid addition salts of acids that are pharmaceutically acceptable.

In the present context, "1:1 salt" indicates a salt comprising 1 eq of the compound of formula [I] and 0.8-1.2 eq of a saltforming acid, such as 1 eq of the compound of formula [I] and 0.9-1.1 eq of a saltforming acid, such as 1 eq of the compound of formula [I] and 0.95-1.05 eq of a saltforming acid, such as 1 eq of the compound of formula [I] and 0.98-1.02 eq of a saltforming acid. In one embodiment, "1:1 salt" indicates a salt comprising 1 eq of the compound of formula [I] and 1 eq of a saltforming acid.

In the present context, "hydrogen adipate" salt of nalmefene refers to the 1:1 salt of the compound of formula [I] and adipic acid.

In the present context, "hydrogen malonate" salt of nalmefene refers to the 1:1 salt of the compound of formula [I] and malonic acid.

In the present context, "lactate" salt of nalmefene refers to the 1:1 salt of the compound of formula [I] and lactic acid. In particular, "DL-lactate" salt of nalmefene refers to the 1:1 salt of the compound of formula [I] and DL-lactic acid. In particular, "D-lactate" salt of nalmefene refers to the 1:1 salt of the compound of formula [I] and D-lactic acid. In particular, "L-lactate" salt of nalmefene refers to the 1:1 salt of the compound of formula [I] and L-lactic acid.

In the present context, "hydrogen fumarate" salt of nalmefene refers to the 1:1 salt of the compound of formula [I] and fumaric acid.

In the present context, "hydrogen succinate" salt of nalmefene refers to the 1:1 salt of the compound of formula [I] and succinic acid.

In the present context, "benzene sulfonate" salt of nalmefene refers to the 1:1 salt of the compound of formula [I] and benzene sulfonic acid.

In the present context, "hydrogen maleate" salt of nalmefene refers to the 1:1 salt of the compound of formula [I] and maleic acid.

In the present context, "salicylate" salt of nalmefene refers to the 1:1 salt of the compound of formula [I] and salicylic acid.

In the present context, by expressions like "crystalline form of a specific salt of nalmefene characterized by the XRPD shown in FIG. 1" is meant the crystalline form of a salt of nalmefene having an XRPD substantially similar to FIG. 1, i.e. exhibiting an XRPD pattern with reflections substantially at the angles as exemplified in that Figure and measured under comparable conditions as described herein or by any comparable method.

In the present context, "Pharmaceutical composition" refers to a solid dose form, such as a solid oral dose form, typically tablets or capsules. "Pharmaceutical compositions of the present invention" refers to all pharmaceutical compositions covered by the claims and description.

In the present context, a "unit dosage form" refers to a formulation unit of a pharmaceutical composition e.g. one tablet or capsule.

In the present context, "therapeutically effective amount" of nalmefene means the amount/dose of nalmefene that is sufficient to produce an effective response (i.e., a biological or medical response of a tissue, system, animal or human sought by a researcher, veterinarian, medical doctor or other clinician) upon administration to a patient. The "therapeutically effective amount" may vary depending on, inter alia, the disease and its severity, and on the age, weight, physical condition and responsiveness of the patient to be treated. Furthermore, the "therapeutically effective amount" may vary if nalmefene is combined with one or more other pharmacologically active compounds; in such a case the amount of nalmefene might be lower, such as a sub-effective amount. In one embodiment, a "therapeutically effective amount" of nalmefene is 18 mg calculated as the free base form.

In the present context, "treatment" and "treating" refers to the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. In one aspect of the present invention, "treatment" and "treating" refers to prophylactic (preventive) treatment. In another aspect, "treatment" and "treating" refers to (curative) treatment. The patient to be treated is preferably a mammal, in particular a human being.

The term "alcohol dependence" is a commonly known term for a skilled person and is described in the revised 4th edition of the Diagnostic and Statistical Manual of Mental Disorders (DSM-IV-TR) (*Diagnostic and Statistical Manual of Mental Disorders*, 4th edition text revision, American Psychiatric Publishing, 2000). As used herein, the term "alcohol dependence" is defined as the presence of three or more of the seven areas of life impairment related to alcohol in the same 12-month period. These impairments include 1) tolerance, 2) withdrawal, 3) the alcohol is often taken in larger amounts or over a longer period than was intended, 4) persistent desire or unsuccessful efforts to cut down or control alcohol intake, 5) a great deal of time is spent in activities necessary to obtain alcohol, intake alcohol, or recover from its effects, 6) important social, occupational, or recreational activities are given up or reduced because of alcohol consumption, 7) alcohol use is continued despite knowledge of having a persistent or recurrent physical or psychological problem that is likely to have been caused or exacerbated by alcohol consumption.

DETAILED DESCRIPTION OF THE INVENTION

The inventor has surprisingly found that certain salts of nalmefene do not form hydrates when precipitated from water and/or said salts do not form solvates when precipitated from organic solvents, such as e.g. EtOH, MeOH, IPA, EtOAc, acetone, ACN, THF, MIBK, toluene and 2,2,2-trifluoroethanol.

The non-hydrate forming nalmefene salts of the present invention have the advantages that they are easy to work with, both from the perspective of chemical production and pharmaceutical production and storage. For example, certain pharmaceutical processes such as granulation by high shear mixing or fluid bed processing implies that the nalmefene salt will be partly or fully dissolved in the granulation liquid. This would, if the nalmefene salt is hydrate forming induce a risk of converting the salt into a hydrated form. Furthermore, the subsequent drying of a granulate implies the risk that a hydrated salt form would lose water and be converted into a less hydrated form. Such changes imply that the stoichiometry can be changed during processing which have certain drawbacks such as the risk of obtaining an end product not fulfilling the specifications.

Pharmaceutical processes implying the risk of either hydrate formation or loss of water from a hydrate are e.g. wet granulation; fluid bed processing; drying at elevated temperature such as at a temperature in the range of 60-90° C.; aqueous based spray drying; aqueous based coating of granules, pellets or tablets; milling at elevated temperature, such as at a temperature in the range of 60-150° C. A non-hydrate forming salt of nalmefene would leave the pharmaceutical processing of the compound with a higher degree of freedom, i.e. leave more options to design the best possible process for the compound.

Also in chemical processing, avoidance of hydrate forming salts could be advantageous from a process point of view as it enables the use of water as a solvent in the purification process and also as a solvent for precipitation without the risk of hydrate formation.

In terms of hydrate formation, the following salts of nalmefene have been shown not to form hydrates when precipitated from pure water at room temperature and atmospheric pressure; the hydrogen adipate salt, the hydrogen malonate salt, the hydrogen fumarate salt, the hydrogen succinate salt, the benzene sulfonate salt, the hydrogen maleate salt and the salicylate salt. This was unexpected, since it is known from literature (Brittain, H. G., *Analytical Profiles of Drug Substances and Excipients;* 1996, Vol. 24: 351-395 and WO 2010/063292) that the HCl salt of nalmefene, the only previously known salt of nalmefene, is only thermodynamically stable in hydrated or solvated form. Further details regarding attempts to form hydrates from nalmefene salts are described in Example 6.

The non-hydrate forming nalmefene salts of the present invention are further characterized by being anhydrous and stable on storage at 40° C./75% RH for at least one week. It is noted that the non-hydrate forming nalmefene salts of the present invention are not hygroscopic; they all absorb less than 1% of water at 90% RH which is reflected by DVS experiments in Example 5, Table 3.

The non-solvate forming nalmefene salts of the present invention implies the advantage in relation to the chemical processing that the lack of solvate formation makes it possible to select the optimal organic solvent for the crystallization process and thereby optimize the purification and yield. It is known from literature (Brittain, H. G., *Analytical Profiles of Drug Substances and Excipients*; 1996, Vol. 24: 351-395), that nalmefene hydrochloride form solvate when precipitated from ethanol.

Solvate formation of the salts of the present invention was assessed in the following solvents: EtOH, MeOH, IPA, EtOAc, acetone, ACN, THF, MIBK, toluene and 2,2,2-trifluoroethanol. No solvates were formed from the following salts when precipitated from various organic solvents at room temperature and atmospheric pressure: the hydrogen adipate salt, the L-lactate salt and the hydrogen maleate salt. The hydrogen malonate salt formed solvate when precipitated from MeOH, the benzene sulfonate salt formed solvate when precipitated from EtOH and THF, and the salicylate salt when precipitated from IPA. Furthermore, it was shown that the hydrogen fumarate and hydrogen succinate salts formed solvate when these were precipitated from 2,2,2-trifluoroethanol (which however, is not a standard solvent commonly used in chemical processes). Even though certain salts of the present invention do form a solvate when precipitated from one particular organic solvent, said salts are not generally prone to solvate formation as they can be precipitated from various other organic solvents without solvate formation. For comparison, it was shown that the hydrochloride salt formed solvate from all the solvents. Further details regarding solvate formation from nalmefene salts are described in Example 7.

Certain salts of the present invention possess additional advantages in terms of aqueous solubility. The aqueous solubility of the salicylate salt is 3 mg base/mL, the aqueous solubility of the hydrogen fumarate salt, the hydrogen maleate salt and the benzene sulfonate salt is in the range of 27-29 mg base/mL, and the aqueous solubility of the hydrogen adipate salt is 65 mg base/mL (see table 4). Thereby, these five salts possess an aqueous solubility that is considerably lower than the aqueous solubility of the known hydrochloride salt of nalmefene which is 109 mg base/mL (unpublished data). This implies the advantages of obtaining a better recovery of the compound from recrystallization from an aqueous solution and furthermore, a salt with low aqueous solubility may facilitate removal of certain impurities with higher solubility.

The aqueous solubility of an active ingredient is also of significance for the choice of dosage form as it may have a direct impact on the formulation of certain dosage forms. Some patients, e.g. elderly patients may have difficulties swallowing tablets, and oral drop solutions may be a suitable alternative avoiding the need for swallowing tablets. In order to limit the volume of an oral drop solution, it is necessary to have a high concentration of the active ingredient in the solution, which again requires a high solubility of the compound. The aqueous solubility of the lactate and the hydrogen succinate salts of nalmefene were found to be 439 and 424 mg base/mL, respectively (Table 4), which is considerably higher than the aqueous solubility of the known hydrochloride salt of nalmefene which is 109 mg base/mL.

In brief, the nalmefene salts of the present invention can be prepared by the following general method. Nalmefene base is added an equivalent amount of the corresponding acid (e.g. adipic acid, malonic acid, L-lactic acid, fumaric acid, succinic acid, benzene sulfonic acid, maleic acid and salicylic acid, respectively) in an appropriate solvent such as IPAc (isopropyl acetate) or EtOH. The suspension is heated to at least 60° C. and subsequently cooled slowly to room temperature. The precipitated salt is isolated and optionally recrystallized in an appropriate solvent such as IPA (Isopropanol). Further details regarding preparation of the salts of the invention are described in Examples 1 and 2.

The nalmefene salts according to the present invention may be used in the preparation of pharmaceutical compositions. Said pharmaceutical compositions may further comprise at least one pharmaceutically acceptable excipient, carrier and/or diluent, and may be in a solid dosage form, such as a tablet, for oral administration. In one embodiment, the invention relates to such pharmaceutical composition.

Methods for the preparation of solid pharmaceutical preparations are well known in the art. See, e.g., Remington: The Science and Practice of Pharmacy, 21st ed., Lippincott Williams & Wilkins (2005). Solid preparations, such as tablets, may be prepared by mixing the active ingredients with an ordinary carrier, such as an adjuvant and/or diluent, and subsequently compressing the mixture in a tableting machine. Non-limiting examples of adjuvants and/or diluents include: corn starch, lactose, talcum, magnesium stearate, gelatine, lactose, gums, and the like. Any other appropriate adjuvant or additive such as colorings, aroma, and preservatives may also be used provided that they are compatible with the active ingredients. The pharmaceutical compositions of the invention thus typically comprise an effective amount of a salt of the present invention and one or more pharmaceutically acceptable carriers.

The nalmefene salts of the present invention may be administered in any suitable way, e.g. orally or parenterally, and they may be presented in any suitable form for such administration, e.g., in the form of tablets, capsules, powders, syrups, oral drop solutions or in the form of solutions or dispersions for injection. In one embodiment, the pharmaceutical composition will comprise a nalmefene salt of the present invention in a therapeutically effective amount.

Preferably, the amount of a nalmefene salt of the present invention in a pharmaceutical composition in unit dosage form is from about 10 mg to about 100 mg, such as from about 10 mg to about 60 mg, e.g. from about 10 mg to about 40 mg, or about 20 mg. In one embodiment, the amount of a nalmefene salt of the present invention in a pharmaceutical composition in unit dosage form corresponds to 18 mg of nalmefene free base.

In particular, it is envisaged that a pharmaceutical composition comprising a nalmefene salt of the present invention may be used for reduction of alcohol consumption in patients with alcohol dependence. In another embodiment, a composition comprising a nalmefene salt of the present invention may be used for the manufacture of a medicament for reduction of alcohol consumption in patients with alcohol dependence. In another embodiment, the invention relates to a method for treating alcohol dependence, comprising administering a therapeutically effective amount of a nalmefene salt of the present invention to a patient in the need thereof.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the various aspects, embodiments, implementations and features of the invention mentioned herein may be claimed separately, or in any combination.

Embodiments According to the Invention

In the following, embodiments of the invention are disclosed. The first embodiment is denoted E1, the second embodiment is denoted E2 and so forth.

E1. A salt of the compound of formula [I]

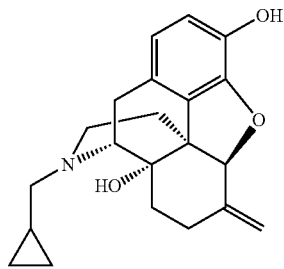

[I]

wherein said salt falls within at least one of the two following categories:
 a) non-hydrate forming salt;
 b) non-solvate forming salt.

E2. The salt according to embodiment 1, which salt is in a solid form.

E3. The salt according to any of embodiments 1-2 which salt is crystalline.

E4. The salt according to any of embodiments 1-3, which salt is selected from the hydrogen adipate salt, the hydrogen malonate salt, the lactate salt, the hydrogen fumarate salt, the hydrogen succinate salt, the benzene sulfonate salt, the hydrogen maleate salt and the salicylate salt of the compound of formula [I].

E5. The salt according to any of embodiments 1-3, wherein said salt is a non-hydrate forming salt.

E6. The salt according to embodiment 5, wherein there is less than 30 mol % water present in the crystal lattice of said salt.

E7. The salt according to embodiment 6, wherein there is less than 25 mol % water, such as less than 20 mol % water, such as less than 15 mol % water, such as less than 10 mol % water, such as less than 5 mol % water, such as less than 4, 3, 2 or 1 mol % water present in the crystal lattice of said salt.

E8. The salt according to any of embodiments 5-7, wherein there is substantially no water present in the crystal lattice of said salt.

E9. The salt according to any of embodiments 5-8, which salt is selected from the hydrogen adipate salt, the hydrogen malonate salt, the hydrogen fumarate salt and the hydrogen succinate salt, the benzene sulfonate salt, the hydrogen maleate salt and the salicylate salt of the compound of formula [I].

E10. The salt according to any of embodiments 1-3, wherein said salt is a non-solvate forming salt.

E11. The salt according to embodiment 10, which salt does not form solvate when precipitated from any of the solvents selected from EtOH, MeOH, IPA, EtOAc, acetone, ACN, THF, MIBK, toluene and 2,2,2-trifluoroethanol.

E12. The salt according to any of embodiments 10-11, which salt is selected from the hydrogen adipate salt, the lactate salt and the hydrogen maleate salt of the compound of formula [I].

E13. The salt according to any of embodiments 1-3, which salt when precipitated from one of the solvents selected from EtOH, MeOH, IPA, EtOAc, acetone, ACN, THF, MIBK, toluene and 2,2,2-trifluoroethanol, does only form solvate from one or two of said solvents.

E14. The salt according to embodiment 13, which salt is selected from the hydrogen malonate salt, the hydrogen fumarate salt, the hydrogen succinate salt, the benzene sulfonate salt and the salicylate salt of nalmefene.

E15. The salt according to any of embodiments 11 or 13, which salt does not form solvate when precipitated from any of the solvents selected from EtOH, IPA, EtOAc, acetone, ACN, THF, MIBK, toluene and 2,2,2-trifluoroethanol.

E16. The salt according to embodiment 15, which salt is selected from the hydrogen adipate salt, the lactate salt, the hydrogen maleate salt and the hydrogen malonate salt of the compound of formula [I].

E17. The salt according to any of embodiments 11 or 13, which salt does not form solvate when precipitated from any of the solvents selected from EtOH, MeOH, IPA, EtOAc, acetone, ACN, THF, MIBK and toluene.

E18. The salt according to embodiment 17, which salt is selected from the hydrogen adipate salt, the lactate salt, the hydrogen maleate salt, the hydrogen fumarate salt and the hydrogen succinate salt of the compound of formula [I].

E19. The salt according to any of embodiments 11 or 13, which salt does not form solvate when precipitated from any of the solvents selected from MeOH, IPA, EtOAc, acetone, ACN, MIBK, toluene and 2,2,2-trifluoroethanol.

E20. The salt according to embodiment 19, which salt is selected from the hydrogen adipate salt, the lactate salt, the hydrogen maleate salt, and the benzene sulfonate salt of the compound of formula [I].

E21. The salt according to any of embodiments 11 or 13, which salt does not form solvate when precipitated from any of the solvents selected from EtOH, MeOH, EtOAc, acetone, ACN, THF, MIBK, toluene and 2,2,2-trifluoroethanol.

E22. The salt according to embodiment 21, which salt is selected from the hydrogen adipate salt, the lactate salt, the hydrogen maleate salt, and the salicylate salt of the compound of formula [I].

E23. The salt according to any of embodiments 1-8 and 10-11, wherein said salt is both a non-hydrate forming salt and a non-solvate forming salt.

E24. The salt according to any of embodiments 1-12 and 15-23, which salt is the hydrogen adipate salt of the compound of formula [I].

E25. The salt according to embodiment 24, which crystal form is characterized by an XRPD obtained using CuK$_{\alpha 1}$ radiation ($\lambda$=1.5406 Å) showing peaks at the following 2θ-angles: 7.66, 11.40, 12.92, 14.90, 15.63, 16.21, 18.22, 18.64, 20.48 and 21.18°.

E26. The salt according to embodiment 25, which crystal form is characterized by an XRPD obtained using CuK$_{\alpha 1}$ radiation ($\lambda$=1.5406 Å) showing peaks at the following 2θ-angles: 7.66, 11.40, 12.92, 14.90 and 16.21°.

E27. The salt according to any of embodiments 24-26, which crystal form is characterized by an XRPD obtained using CuK$_{\alpha 1}$ radiation ($\lambda$=1.5406 Å) as depicted in FIG. 1.

E28. The salt according to any of embodiments 24-27, which crystal form is characterized by having a DSC trace showing an endotherm with onset about 179° C.

E29. The salt according to any of embodiments 1-9 and 13-16 which salt is the hydrogen malonate salt of the compound of formula [I].

E30. The salt according to embodiment 29, which crystal form is characterized by an XRPD obtained using CuK$_{\alpha 1}$ radiation ($\lambda$=1.5406 Å) showing peaks at the following 2θ-angles: 10.48, 10.74, 11.31, 11.92, 12.14, 14.40, 15.43, 15.61, 16.63 and 21.03°.

E31. The salt according to embodiment 30, which crystal form is characterized by an XRPD obtained using CuK$_{\alpha 1}$ radiation ($\lambda$=1.5406 Å) showing peaks at the following 2θ-angles: 10.48, 10.74, 11.31, 11.92 and 12.14°.

Figure 2:
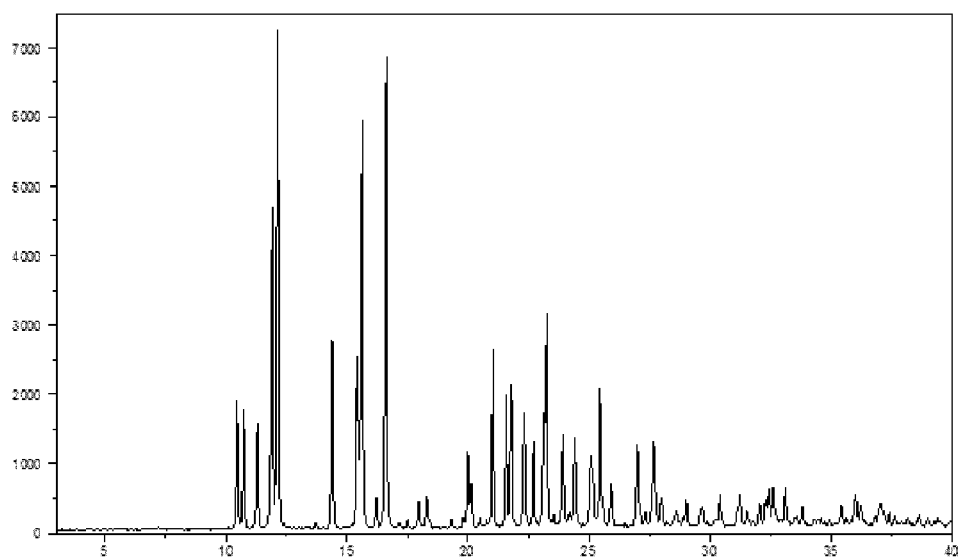
FIG. 2: XRPD pattern of the hydrogen malonate salt of nalmefene.

E32. The salt according to any of embodiments 29-31, which crystal form is characterized by an XRPD obtained using CuK$_{\alpha 1}$ radiation ($\lambda$=1.5406 Å) as depicted in FIG. 2.

E33. The salt according to any of embodiments 29-32, which crystal form is characterized by having a DSC trace showing an endotherm with onset about 191° C. (degradation).

E34. The salt according to any of embodiments 1-4, 10-12 and 15-22, which salt is the lactate salt of the compound of formula [I].

E35. The salt according to embodiment 34, which salt is the DL-lactate salt of the compound of formula [I].

E36. The salt according to embodiment 34, which salt is the D-lactate salt of the compound of formula [I].

E37. The salt according to embodiment 34, which salt is the L-lactate salt of the compound of formula [I].

E38. The salt according to embodiment 37, which crystal form is characterized by an XRPD obtained using CuK$_{\alpha 1}$ radiation ($\lambda$=1.5406 Å) showing peaks at the following 2θ-angles: 10.41, 11.16, 11.80, 12.46, 15.23, 15.85, 16.64, 19.23, 19.71 and 20.11°.

E39. The salt according to embodiment 38, which crystal form is characterized by an XRPD obtained using CuK$_{\alpha 1}$ radiation ($\lambda$=1.5406 Å) showing peaks at the following 2θ-angles: 10.41, 11.16, 11.80, 12.46 and 15.85°.

Figure 3:
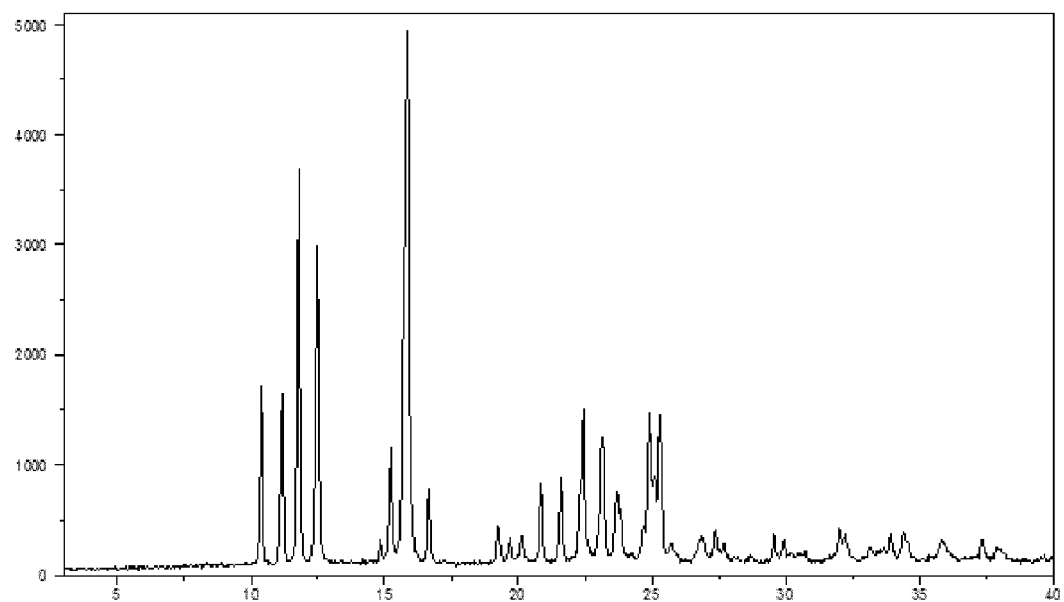
FIG. 3: XRPD pattern of the L-lactate salt of nalmefene.

E40. The salt according to any of embodiments 37-39, which crystal form is characterized by an XRPD obtained using CuK$_{\alpha 1}$ radiation ($\lambda$=1.5406 Å) as depicted in FIG. 3.

E41. The salt according to any of embodiments 37-40, which crystal form is characterized by having a DSC trace showing an endotherm with onset about 183° C. (degradation).

E42. The salt according to any of embodiments 1-9, 13-14 and 17-18, which salt is the hydrogen fumarate salt of the compound of formula [I].

E43. The salt according to embodiment 42, which crystal form is characterized by an XRPD obtained using CuK$_{\alpha 1}$ radiation ($\lambda$=1.5406 Å) showing peaks at the following 2θ-angles: 8.00, 10.90, 13.04, 13.70, 14.90, 16.95, 17.68, 18.34, 18.85 and 20.77°.

E44. The salt according to embodiment 43, which crystal form is characterized by an XRPD obtained using CuK$_{\alpha 1}$ radiation ($\lambda$=1.5406 Å) showing peaks at the following 2θ-angles: 8.00, 10.90, 13.04, 13.70 and 14.90°.

Figure 4:
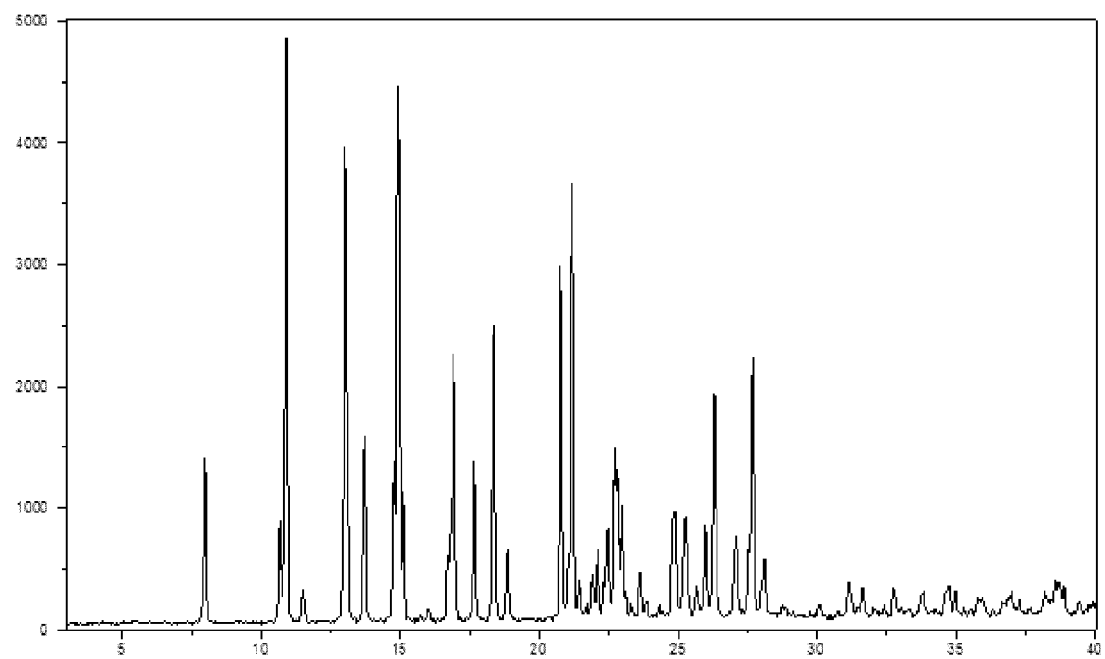
FIG. 4: XRPD pattern of the hydrogen fumarate salt of nalmefene.

E45. The salt according to any of embodiments 42-44, which crystal form is characterized by an XRPD obtained using CuK$_{\alpha 1}$ radiation ($\lambda$=1.5406 Å) as depicted in FIG. 4.

E46. The salt according to any of embodiments 42-45, which crystal form is characterized by having a DSC trace showing an endotherm with onset about 254° C. (degradation).

E47. The salt according to any of embodiments 1-9, 13-14 and 17-18, which salt is the hydrogen succinate salt of the compound of formula [I].

E48. The salt according to embodiment 47, which crystal form is characterized by an XRPD obtained using CuK$_{\alpha 1}$ radiation ($\lambda$=1.5406 Å) showing peaks at the following 2θ-angles: 8.03, 10.72, 10.90, 11.52, 13.00, 13.70, 14.79, 16.86, 17.72 and 18.26°.

E49. The salt according to embodiment 48, which crystal form is characterized by an XRPD obtained using CuK$_{\alpha 1}$ radiation ($\lambda$=1.5406 Å) showing peaks at the following 2θ-angles: 8.03, 10.90, 13.00, 13.70 and 14.79°.

Figure 5:
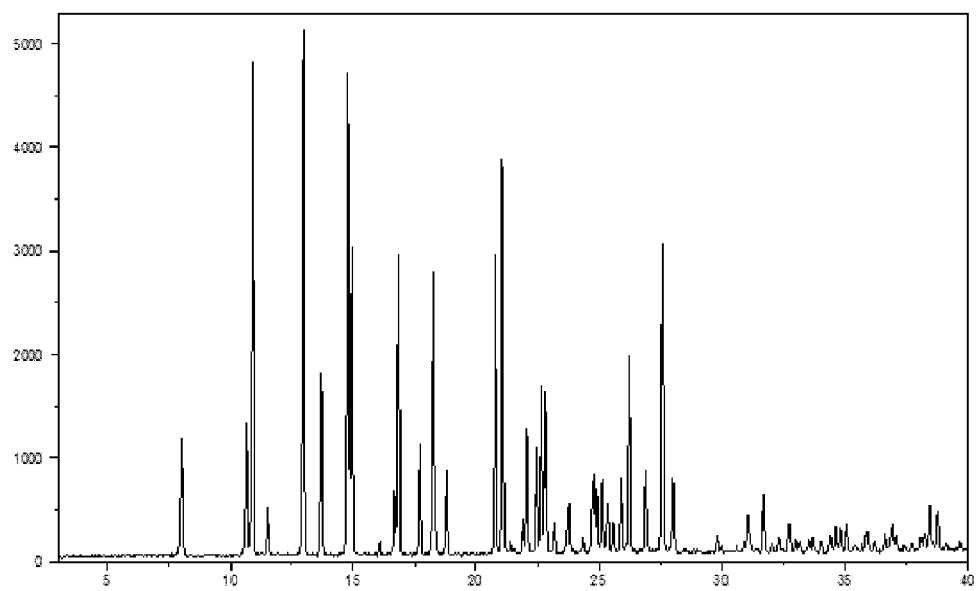
FIG. 5: XRPD pattern of the hydrogen succinate salt of nalmefene.

E50. The salt according to any of embodiments 47-49, which crystal form is characterized by an XRPD obtained using CuK$_{\alpha 1}$ radiation ($\lambda$=1.5406 Å) as depicted in FIG. 5.

E51. The salt according to any of embodiments 47-50, which crystal form is characterized by having a DSC trace showing an endotherm with onset about 188° C.

E52. The salt according to any of embodiments 1-9, 13-14 and 19-20, which salt is the benzene sulfonate salt of the compound of formula [I].

E53. The salt according to embodiment 52, which crystal form is characterized by an XRPD obtained using CuK$_{\alpha 1}$ radiation ($\lambda$=1.5406 Å) showing peaks at the following 2θ-angles: 7.07, 10.77, 13.42, 13.62, 14.98, 16.34, 17.06, 17.79, 19.64 and 20.39°.

E54. The salt according to embodiment 53 which crystal form is characterized by an XRPD obtained using CuK$_{\alpha 1}$ radiation ($\lambda$=1.5406 Å) showing peaks at the following 2θ-angles: 1.07, 10.77, 13.42, 13.62, 14.98 and 16.34°.

Figure 6:
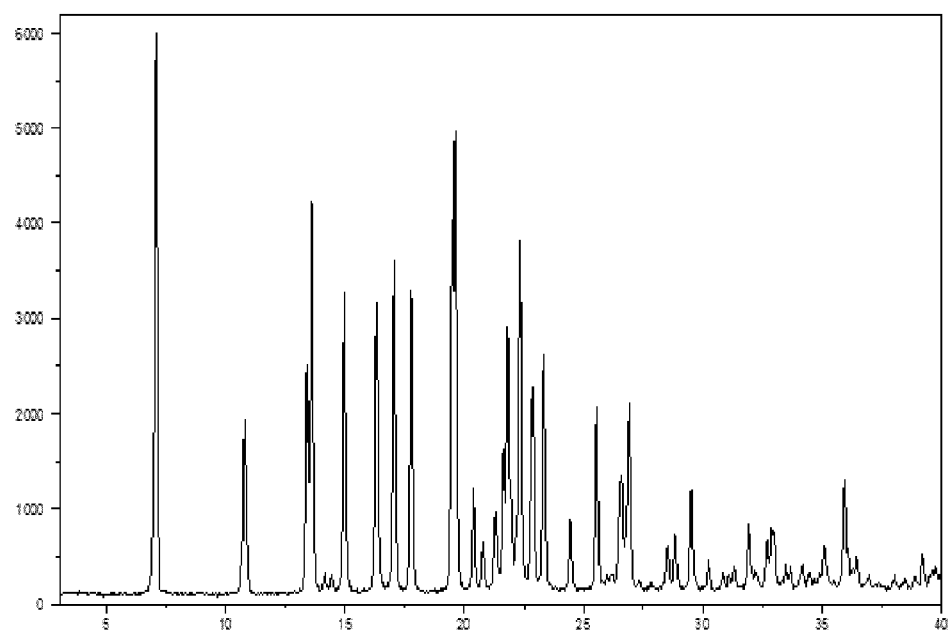
FIG. 6: XRPD pattern of the benzene sulfonate salt of nalmefene.

E55. The salt according to any of embodiments 52-54, which crystal form is characterized by an XRPD obtained using CuK$_{\alpha 1}$ radiation ($\lambda$=1.5406 Å) as depicted in FIG. 6.

E56. The salt according to any of embodiments 52-55, which crystal form is characterized by having a DSC trace showing an endotherm with onset about 222° C.

E57. The salt according to any of embodiments 1-12 and 15-23, which salt is the hydrogen maleate salt of the compound of formula [I].

E58 The salt according to embodiment 57, which crystal form is characterized by an XRPD obtained using CuK$_{\alpha 1}$ radiation ($\lambda$=1.5406 Å) showing peaks at the following 2θ-angles: 7.64, 10.59, 11.03, 11.81, 12.94, 14.92, 15.32, 15.92, 16.13 and 16.86°.

E59. The salt according to embodiment 58 which crystal form is characterized by an XRPD obtained using CuK$_{\alpha 1}$ radiation ($\lambda$=1.5406 Å) showing peaks at the following 2θ-angles: 7.64, 10.59, 12.94, 14.92 and 15.32°.

Figure 7:
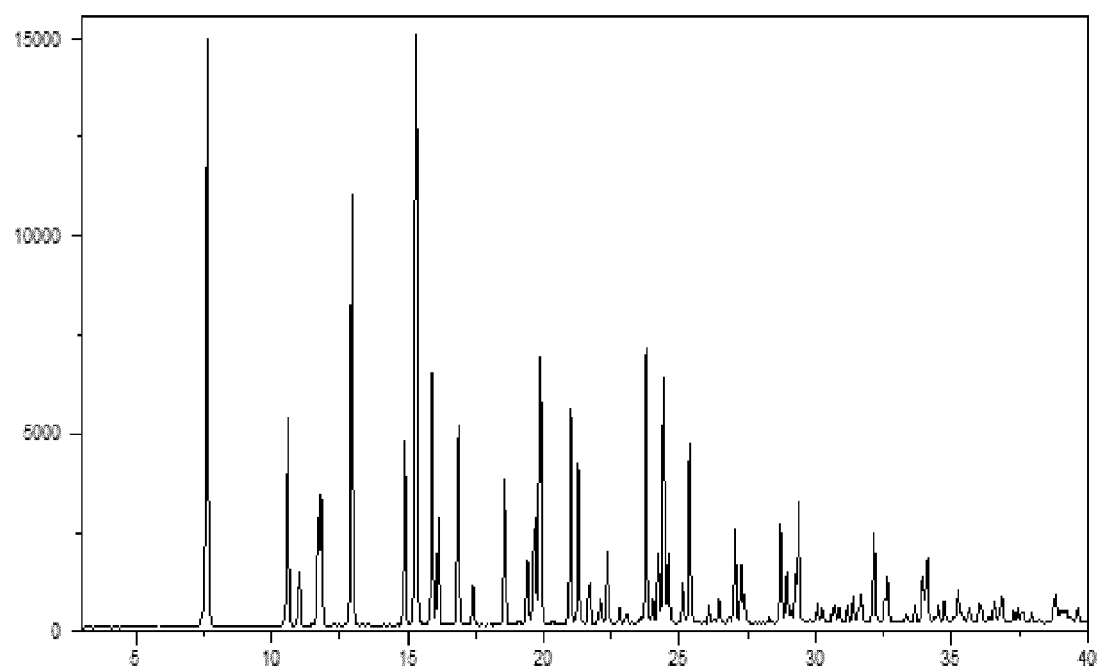
FIG. 7: XRPD pattern of the hydrogen maleate salt of nalmefene.

E60. The salt according to any of embodiments 57-59, which crystal form is characterized by an XRPD obtained using CuK$_{\alpha 1}$ radiation ($\lambda$=1.5406 Å) as depicted in FIG. 7.

E61. The salt according to any of embodiments 57-60, which crystal form is characterized by having a DSC trace showing an endotherm with onset about 213° C. (degradation).

E62. The salt according to any of embodiments 1-9, 13-14 and 21-22, which salt is the salicylate salt of the compound of formula [I].

E63. The salt according to embodiment 62, which crystal form is characterized by an XRPD obtained using CuK$_{\alpha 1}$ radiation ($\lambda$=1.5406 Å) showing peaks at the following 2θ-angles: 8.44, 9.78, 11.08, 12.16, 13.21, 14.40, 16.24, 16.71, 17.43 and 19.62°.

E64. The salt according to embodiment 63 which crystal form is characterized by an XRPD obtained using CuK$_{\alpha 1}$ radiation ($\lambda$=1.5406 Å) showing peaks at the following 2θ-angles: 8.44, 9.78, 11.08, 12.16 and 13.21°.

Figure 8:
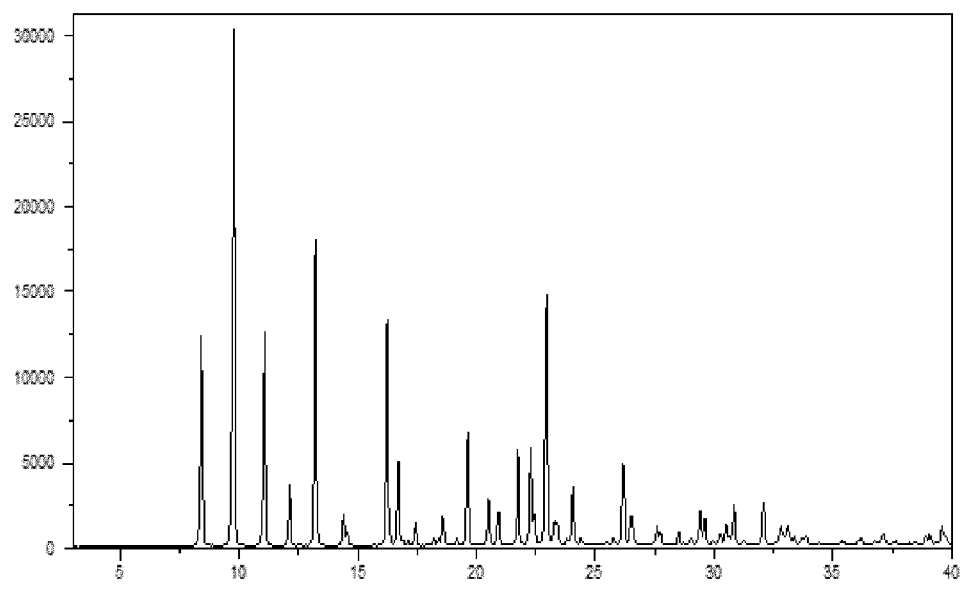
FIG. 8: XRPD pattern of the salicylate salt of nalmefene. TGA and DSC profiles of nalmefene salts are shown in FIGS. 9-16. The X axis shows the temperature (° C.), the left hand y-axis shows the TGA weight loss (%), the right hand y-axis shows the DSC heat flow (W/g).
Figure 9:
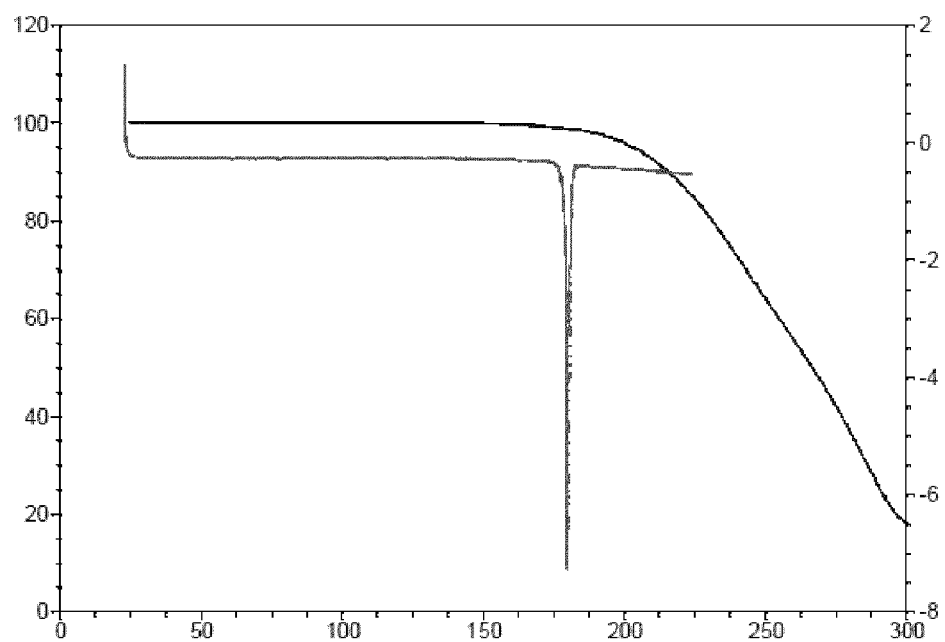
FIG. 9: TGA and DSC thermograms of the hydrogen adipate salt of nalmefene.
Figure 10:
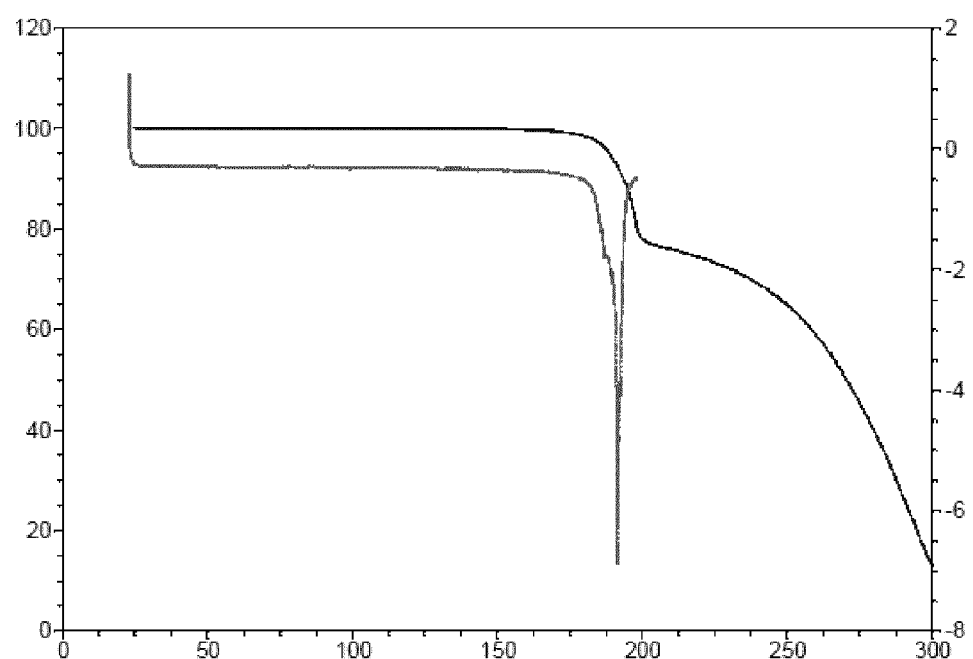
FIG. 10: TGA and DSC thermograms of the hydrogen malonate salt of nalmefene.
Figure 11:
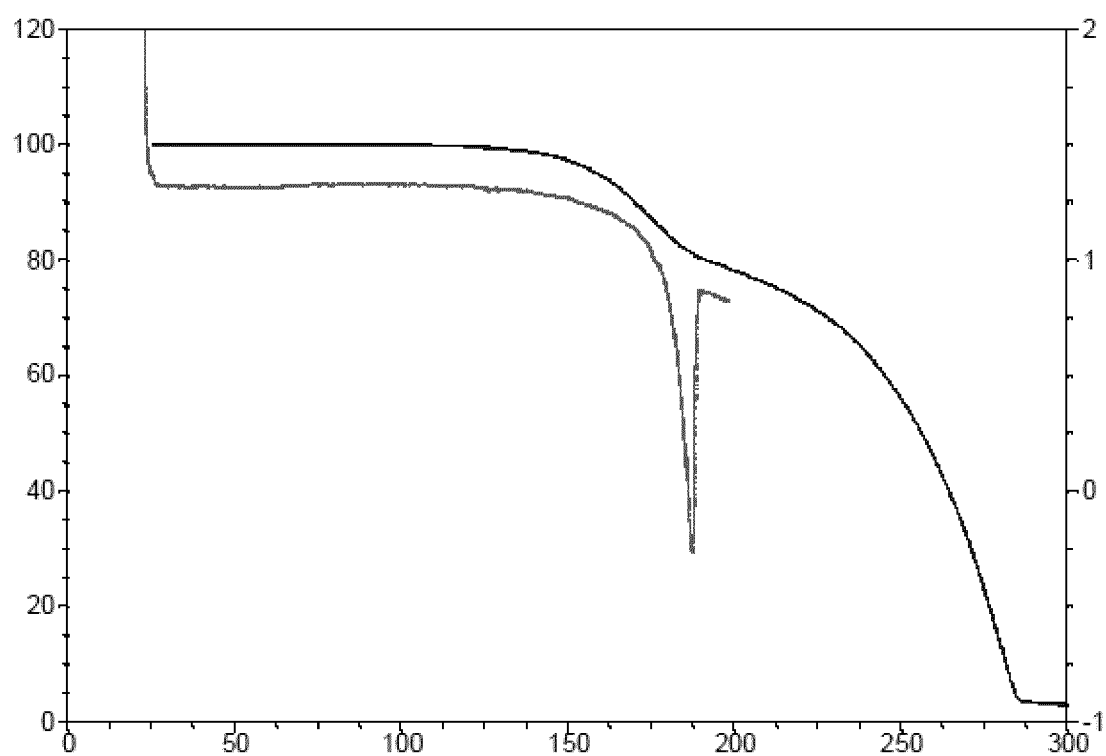
FIG. 11: TGA and DSC thermograms of the L-lactate salt of nalmefene.
Figure 12:
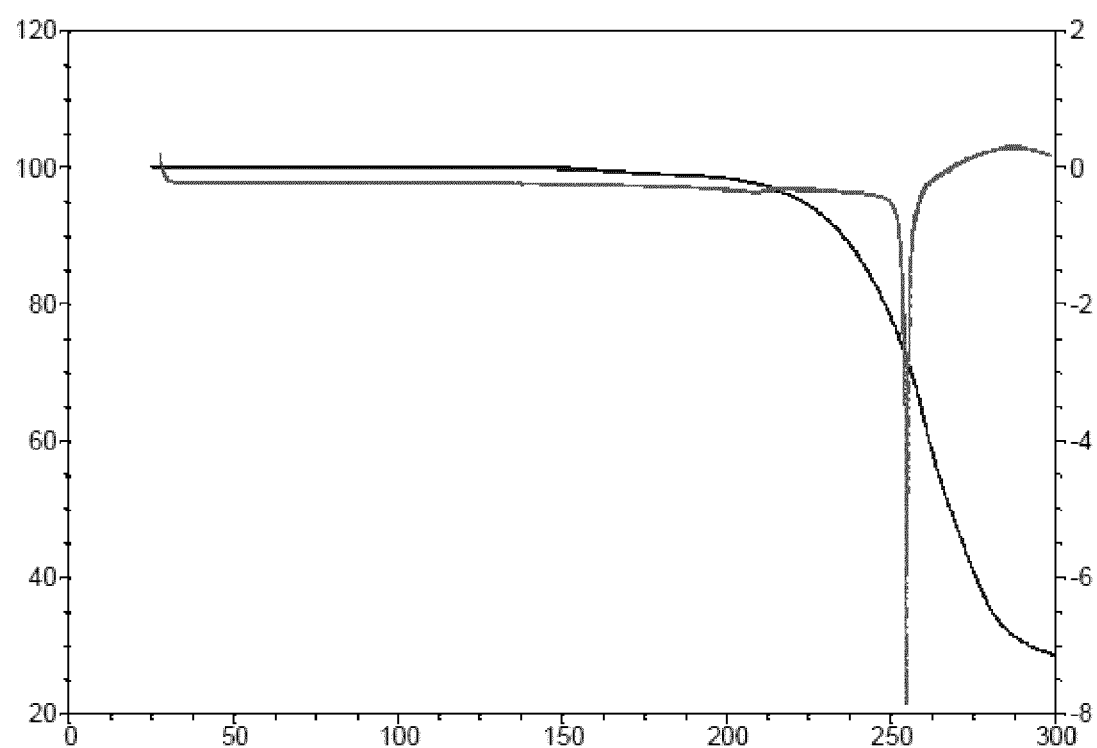
FIG. 12: TGA and DSC thermograms of the hydrogen fumarate salt of nalmefene.
Figure 13:
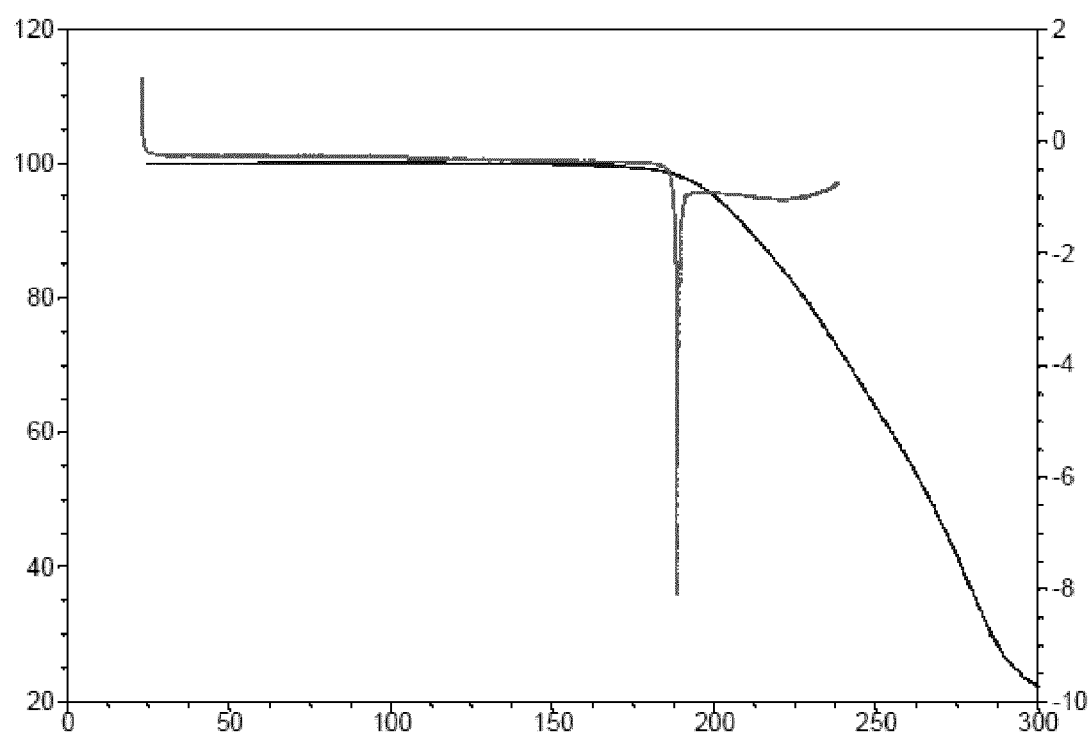
FIG. 13: TGA and DSC thermograms of the hydrogen succinate salt of nalmefene.
Figure 14:
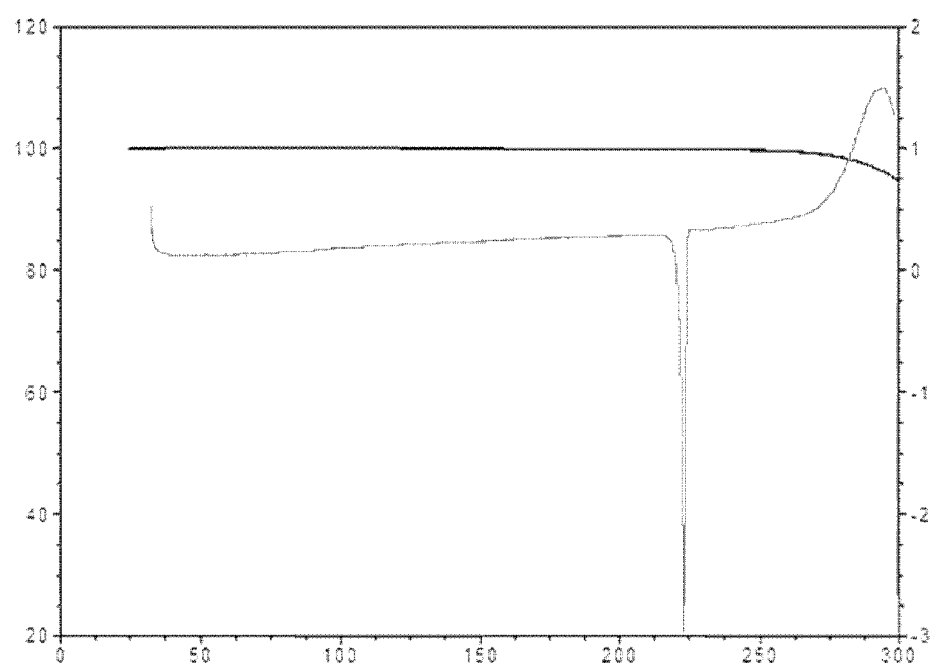
FIG. 14: TGA and DSC thermograms of the benzene sulfonate salt of nalmefene.
Figure 15:
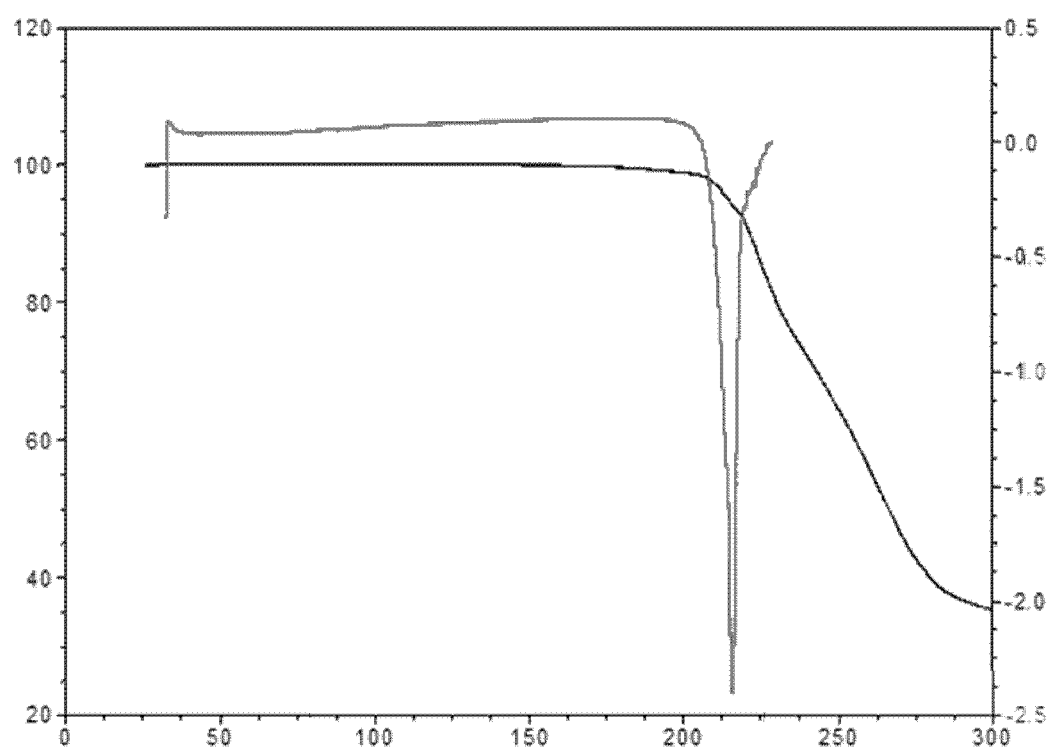
FIG. 15: TGA and DSC thermograms of the hydrogen maleate salt of nalmefene.
Figure 16:
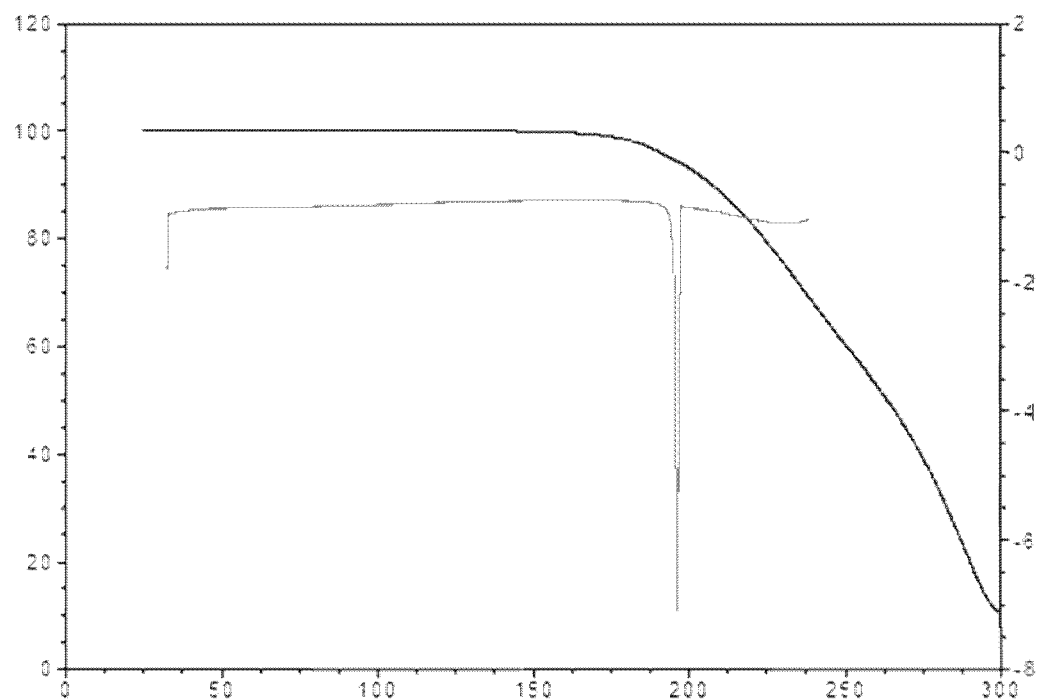
FIG. 16: TGA and DSC thermograms of the salicylate salt of nalmefene.
Figure 17:
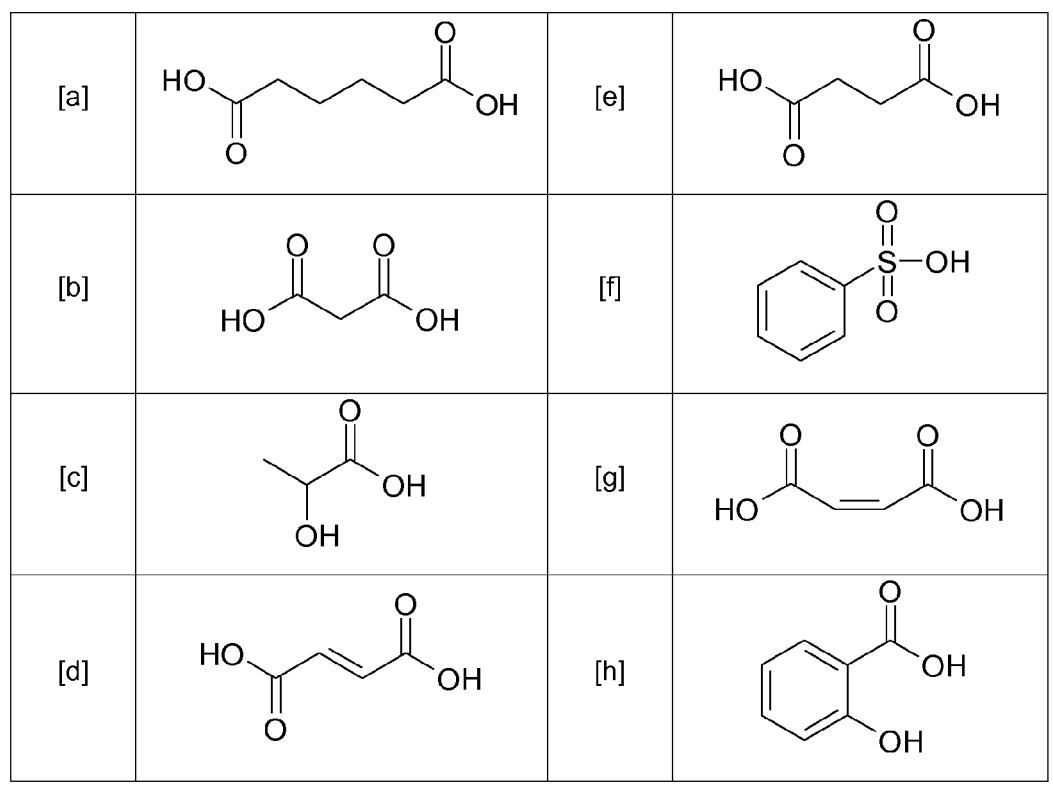
FIG. 17: Table with structural formulas of [a]: adipic acid, [b]: malonic acid, [c]: lactic acid, [d]: fumaric acid, [e]: succinic acid, [f]: benzene sulfonic acid, [g]: maleic acid, [h]: salicylic acid.

E65. The salt according to any of embodiments 62-64, which crystal form is characterized by an XRPD obtained using CuK$_{\alpha 1}$ radiation ($\lambda$=1.5406 Å) as depicted in FIG. 8.

E66. The salt according to any of embodiments 62-65, which crystal form is characterized by having a DSC trace showing an endotherm with onset about 196° C.

E67. A pharmaceutical composition comprising a salt according to any of embodiments 1-66.

E68. The pharmaceutical composition according to embodiment 67, characterized in that said composition are manufactured by a process comprising one or more of the process steps selected from wet granulation, fluid bed processing, drying at elevated temperature such as at a temperature above room temperature, aqueous based spray drying, aqueous based coating of granules, pellets or tablets, milling at elevated temperature.

E69. A salt according to any of embodiments 1-66 for use as a medicament.

E70. A salt according to any of embodiments 1-66 for use in therapy.

E71. A salt according to any of embodiments 1-66 or a pharmaceutical composition according to any embodiments 67-68 for use reduction of alcohol consumption in a patient with alcohol dependence.

E72. A method for the reduction of alcohol consumption in a patient with alcohol dependence, which method comprises the administration of a therapeutically effective amount of a salt according to any of embodiments 1-66 to said patient.

EXAMPLES

The invention will be illustrated by the following non-limiting examples.

Example 1

Preparation of the Hydrogen Adipate Salt, the Hydrogen Malonate Salt, the Lactate Salt, the Hydrogen Fumarate Salt and the Hydrogen Succinate Salt of Nalmefene To nalmefene base (5.5 g) was added one molar equivalent of the corresponding acid (adipic acid, malonic acid, L-lactic acid, fumaric acid or succinic acid, respectively) in IPAc (125 mL isopropyl acetate). The suspension was heated to at least 60° C. (not completely dissolved) and subsequently allowed to cool slowly to room temperature.

The first batch of the nalmefene hydrogen malonate salt contained an excess of the free base, and the first batch of the nalmefene hydrogen fumarate salt contained excess of fumaric acid as seen by XRPD. These two batches were then recrystallized in IPA.

Example 2

Preparation of the Benzene Sulfonate Salt, the Hydrogen Maleate Salt and the Salicylate Salt of Nalmefene Benzene sulfonate: A mixture of nalmefene free base (5.0 g) and one molar equivalent of benzene sulfonic acid in 25 mL EtOH was heated to reflux whereby all dissolved. The mixture was allowed to cool slowly to room temperature. As no precipitation occurred after 1 h, seed material was obtained by adding a few drops of IPAc to in total 1 mL of the solution in a small tube. This gave a precipitate, which was then added to reaction mixture, leading to subsequent crystallization. The mixture was stirred at room temperature for 2-3 h. The resulting salt was isolated by filtration and washed with a small amount of ethanol and dried under vacuum at 50° C. overnight. The resulting salt was a solvate. This was subsequently suspended in water with stirring for a few hours, and subsequently filtered and dried under vacuum. This precipitate was found to be solvent free.

Maleate and salicylate: A mixture of nalmefene free base (5.0 g) and one molar equivalent of the corresponding acid (maleic acid or salicylic acid) in isopropyl acetate (50 mL) was heated to reflux and then allowed to cool slowly to room temperature. Precipitation occurred, and the mixture was stirred at room temperature for 2-3 h. The precipitate was isolated by filtration, washed with a small amount of isopropyl acetate and dried under vacuum at 50° C. overnight. The hydrogen maleate salt showed some extra reflections in the XRPD and extra endotherms in DSC. After being slurried in water (for determination of the solubility in water) these extra reflections/endotherms disappeared.

Example 3

XRPD Characterization

X-Ray powder diffractograms were measured on a PANalytical X'Pert PRO X-Ray Diffractometer using CuK$_{\alpha 1}$ radiation. The samples were measured in reflection mode in the 2θ-range 2-40° using an X'celerator detector. XRPD patterns of the hydrogen adipate, hydrogen malonate, L-lactate, hydrogen fumarate, hydrogen succinate, benzene sulfonate, hydrogen maleate and salicylate salts are shown in FIGS. 1-8 and characteristic main peaks are listed in Table 1 below.

TABLE 1

Characteristic XRPDs on salts of nalmefene, obtained using CuK$_{\alpha1}$ radiation ($\lambda$ = 1.5406 Å) showing peaks at the following 2θ-angles

| Salt | Characteristic main peaks (expressed in degree of diffraction angle 2θ) |
| --- | --- |
| Hydrogen adipate | 7.66, 11.40, 12.92, 14.90, 15.63, 16.21, 18.22, 18.64, 20.48, 21.18 |
| Hydrogen malonate | 10.48, 10.74, 11.31, 11.92, 12.14, 14.40, 15.43, 15.61, 16.63, 21.03 |
| L-lactate | 10.41, 11.16, 11.80, 12.46, 15.23, 15.85, 16.64, 19.23, 19.71, 20.11 |
| Hydrogen Fumarate | 8.00, 10.90, 13.04, 13.70, 14.90, 16.95, 17.68, 18.34, 18.85, 20.77 |
| Hydrogen succinate | 8.03, 10.72, 10.90, 11.52, 13.00, 13.70, 14.79, 16.86, 17.72, 18.26 |
| Benzene sulfonate | 7.07, 10.77, 13.42, 13.62, 14.98, 16.34, 17.06, 17.79, 19.64, 20.39 |
| Hydrogen maleate | 7.64, 10.59, 11.03, 11.81, 12.94, 14.92, 15.32, 15.92, 16.13, 16.86 |
| Salicylate | 8.44, 9.78, 11.08, 12.16, 13.21, 14.40, 16.24, 16.71, 17.43, 19.62 |

Example 4

Thermal Analysis

The Differential Scanning Calorimetry (DSC) measurements are performed using equipment TA-Instruments DSC-Q2000 calibrated at 5°/min to give the melting point as onset value. About 2 mg of sample is heated 5°/min under nitrogen flow in a closed pan with a pinhole in the lid.

Thermo gravimetric analysis (TGA) is performed using a TA-instruments TGA-Q500. 1-10 mg sample is heated 10°/min in an open pan under nitrogen flow.

TGA and DSC thermograms of the hydrogen adipate, hydrogen malonate, L-lactate, hydrogen fumarate, hydrogen succinate, benzene sulfonate, hydrogen maleate and salicylate salts are shown in FIGS. 9-16 and DSC data are shown in Table 2 below.

TABLE 2

DSC data of salts of nalmefene

| Salt | DSC endotherm onset (° C.) | DSC endotherm peak (° C.) | dH (J/g) |
| --- | --- | --- | --- |
| Hydrogen adipate | 179.4 | 179.8 | 124 |
| Hydrogen malonate | 191.1 | 191.5 | 256 |
| L-lactate | 182.5 | 187.4 | 72 |
| Hydrogen Fumarate | 254.0 | 254.4 | 157 |
| Hydrogen succinate | 188.4 | 188.4 | 108 |
| Benzene sulfonate | 222.0 | 223.0 | 75 |
| Hydrogen maleate | 213.4 | 215.7 | 167 |
| Salicylate | 195.6 | 196.2 | 107 |

Example 5

DVS Experiments

Dynamic vapour sorption experiments were performed using a SMS DVS advantage 01 changing the relative humidity from 30-40% RH up to 90-95% RH in steps of 10% RH. Data are shown in Table 3 below.

TABLE 3

Water absorption at 90% RH determined by DVS.

| Salt | % abs. at 90% RH |
| --- | --- |
| Hydrogen adipate | 0.35% |
| Hydrogen malonate | 0.35% |
| L-lactate | 1.2% |
| Hydrogen Fumarate | 0.6% |
| Hydrogen succinate | <0.1% |
| Benzene sulfonate | <0.2% |
| Hydrogen maleate | 0.2% |
| Salicylate | 0.4% |

Example 6

Determination of Aqueous Solubility and Attempt to Form Hydrates

Thermodynamic solubility of the hydrogen adipate, hydrogen malonate, L-lactate, hydrogen fumarate, hydrogen succinate, benzene sulfonate, hydrogen maleate and salicylate salts was measured by shaking an excess amount of the eight nalmefene salts in pure water in a sealed container at a constant temperature at room temperature (23° C.±2°). After equilibrium was attained, a sample was withdrawn, the solid filtered or centrifuged off, and the clear filtrate/supernatant was diluted and assayed by HPLC. The experiments with hydrogen succinate and L-lactate led to complete dissolution in the first determination. These solutions were left for evaporation of the water leading to an oil. These experiments were subsequently repeated using a larger amount of solid. Except for L-lactate all precipitates were the same as the initial compound, thus no hydrates were formed. The L-lactate led to a precipitate with a different XRPD than the initial compound and TGA showed a weight loss of 4.0% up to 135° C. which corresponds to a monohydrate.

Aqueous solubility of the nalmefene salts are listed in Table 4. All solubilities are normalised to the relative solubility of nalmefene free base.

TABLE 4

Aqueous solubility of salts of nalmefene at 23° C. ± 2°

| Salt | pH | Solubility (mg base/mL) |
| --- | --- | --- |
| Hydrogen adipate | 4.72 | 65 |
| Hydrogen malonate | 4.08 | 130 |
| L-lactate | 5.64 | 439 |
| Hydrogen Fumarate | 3.49 | 27 |
| Hydrogen succinate | 4.61 | 424 |
| Benzene sulfonate | 3.12 | 28 |
| Hydrogen maleate | 5.93 | 29 |
| Salicylate | 7.14 | 3.0 |

Example 7

Determination of Solubility in Organic Solvents and Attempt to Form Solvates The solubility of the hydrogen adipate, hydrogen malonate, L-lactate, hydrogen fumarate and hydrogen succinate, benzene sulfonate, hydrogen maleate and salicylate salts was determined in the following organic solvents: EtOH, MeOH, IPA, EtOAc, acetone, ACN, THF, MIBK, toluene and 2,2,2-trifluoroethanol. The suspensions were heated with the purpose of obtaining complete dissolution and then cooled to room temperature and left for equilibrium to be attained. The clear supernatant was diluted and assayed by HPLC. All precipitates were analyzed by XRPD. Except for hydrogen malonate in MeOH, benzene sulfonate in EtOH and THF, hydrogen fumarate and hydrogen succinate in 2,2,2-trifluoroethanol and salicylate in IPA, all precipitates were the same crystal form as the initial material, thus no solvates were formed.

For comparison, the solvate formation from nalmefene hydrochloride was also investigated. It was shown that the hydrochloride salt formed solvate from all the organic solvents (EtOH, MeOH, IPA, EtOAc, acetone, ACN, THF, MIBK, toluene and 2,2,2-trifluoroethanol). Solubilities of the nalmefene salts in organic solvents are listed in Table 5. All solubilities are normalised to the relative solubility of nalmefene free base.

TABLE 5

Solubility of salts of nalmefene in organic solvents at 23° C. ± 2° (mg base/mL)

| Salt | EtOH | MeOH | IPA | EtOAc | acetone | ACN |
|---|---|---|---|---|---|---|
| Hydrogen adipate | 27 | 143 | 8.3 | 2.1 | 6.0 | 1.85 |
| Hydrogen malonate | 26 | 167* | 11 | 0.7 | 2.7 | 10 |
| L-lactate | 143 | 299 | 31 | 5.3 | 11.9 | 9.2 |
| Hydrogen Fumarate | 16 | 73 | 2.5 | 3.6 | 0.67 | 0.22 |
| Hydrogen succinate | 51 | 237 | 11 | 1.6 | 6.84 | 4.7 |
| Benzene sulfonate | 13* | 152 | 3.1 | 0.14 | 2.5 | 26 |
| Hydrogen maleate | 48 | 121 | 3.4 | 0.55 | 3.7 | 12 |
| Salicylate | 19 | 91 | 0.5* | 2.0 | 9.7 | 8.2 |

| Salt | THF | MIBK | toluene | 2,2,2-trifluoro-EtOH |
|---|---|---|---|---|
| Hydrogen adipate | 65 | 2.6 | 0.21 | 236 |
| Hydrogen malonate | 4.9 | 0.73 | 0.13 | 325 |
| L-lactate | 44.5 | 5.2 | 0.43 | >370 |
| Hydrogen Fumarate | 6.6 | 0.1 | 0.01 | 24* |
| Hydrogen succinate | 29 | 1.6 | 0.13 | 154* |
| Benzene sulfonate | 0.35 | 0.19 | n.a. | 314 |
| Hydrogen maleate | 2.1 | 0.64 | n.a. | 248 |
| Salicylate | 35 | 2.9 | n.a. | 120 |

*precipitated as solvate
n.a.: not available,
n.d.: not detected

HPLC analysis of solubility samples according to Examples 6 and 7 was performed on an X-bridge C-18 column using 25 mM phosphate buffer pH 6.0/MeOH 50/50 as mobile phase and UV detection at 230 nm.

The invention claimed is:
1. A salt of the compound of formula [I]

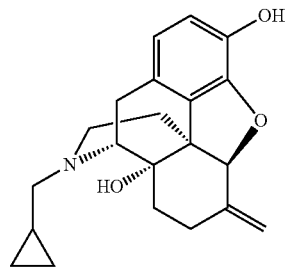

[I]

wherein said salt is crystalline and wherein said salt falls within at least one of the two following categories:

(a) a salt wherein water molecules do not form part of the crystal lattice of said salt when said salt is precipitated from water at atmospheric pressure and in a temperature range between 15-30° C.; and
(b) a salt wherein solvent molecules do not form part of the crystal lattice of said salt when said salt is precipitated from a solvent selected from the group consisting of: EtOH, MeOH, IPA, EtOAc, acetone, ACN, THF, MIBK, toluene and 2,2,2-trifluoroethanol, at atmospheric pressure and in a temperature range between 15-30° C.

2. The salt according to claim 1, wherein said salt is selected from the group consisting of: the hydrogen adipate salt, the hydrogen malonate salt, the lactate salt, the hydrogen fumarate salt, the hydrogen succinate salt, the benzene sulfonate salt, the hydrogen maleate salt and the salicylate salt of the compound of formula [I].

3. The salt according to claim 1, wherein said salt falls at least within category (a).

4. The salt according to claim 3, of which salt any isolated crystal form contains less than 30 mol % water in the crystal lattice of said salt.

5. The salt according to claim 4, of which salt any isolated crystal form contains less than 25 mol % water present in the crystal lattice of said salt.

6. The salt according to claim 1, wherein said salt falls at least within category (b).

7. The salt according to claim 6, wherein when said salt is precipitated from a solvent selected from said group at least one of said formed crystal lattices does not include solvent.

8. The salt according to claim 1, wherein said salt falls within both category (a) and category (b).

9. A pharmaceutical composition comprising the salt according to claim 1.

10. The pharmaceutical composition according to claim 9, wherein said composition is manufactured by a process comprising one or more process steps selected from the group consisting of:
 (1) wet granulation,
 (2) fluid bed processing,
 (3) drying at elevated temperature,
 (4) aqueous based spray drying,
 (5) aqueous based coating of granules, pellets or tablets, and
 (6) milling at elevated temperature.

11. A method of treatment of alcohol dependence, wherein said method comprises administering the pharmaceutical composition of claim 9 to a subject in need thereof.

12. The method of treatment of claim 11, wherein said subject suffers from alcohol dependence and said treatment reduces alcohol consumption.

13. The salt according to claim 1, wherein said salt falls within at least one of the two following categories:
 (a) a salt wherein water molecules do not form part of the crystal lattice of said salt when said salt is precipitated from water at atmospheric pressure in a temperature range between 20-25° C.; and
 (b) a salt wherein solvent molecules do not form part of the crystal lattice of said salt when said salt is precipitated from a solvent selected from the group consisting of: EtOH, MeOH, IPA, EtOAc, acetone, ACN, THF, MIBK, toluene and 2,2,2-trifluoroethanol, at atmospheric pressure and in a temperature range between 20-25° C.

14. The salt according to claim 6, wherein when said salt is precipitated from a solvent selected from said group none of said formed crystal lattices includes solvent.

\* \* \* \* \*